US011076976B2

(12) United States Patent
Benhabiles

(10) Patent No.: US 11,076,976 B2
(45) Date of Patent: Aug. 3, 2021

(54) POSTURE SAVER

(71) Applicant: Mustapha Benhabiles, Huntington Beach, CA (US)

(72) Inventor: Mustapha Benhabiles, Huntington Beach, CA (US)

( * ) Notice: Subject to any disclaimer, the term of this patent is extended or adjusted under 35 U.S.C. 154(b) by 0 days.

(21) Appl. No.: 16/705,241

(22) Filed: Dec. 6, 2019

(65) Prior Publication Data

US 2021/0169676 A1 Jun. 10, 2021

(51) Int. Cl.
*A61F 5/02* (2006.01)
*A41D 1/04* (2006.01)

(52) U.S. Cl.
CPC ............... *A61F 5/026* (2013.01); *A41D 1/04* (2013.01); *A41D 2300/32* (2013.01); *A41D 2300/322* (2013.01); *A41D 2300/324* (2013.01); *A41D 2300/326* (2013.01); *A41D 2300/328* (2013.01); *A41D 2300/33* (2013.01); *A41D 2300/332* (2013.01); *A41D 2400/32* (2013.01)

(58) Field of Classification Search
CPC .. A61F 5/028; A61F 5/02; A61F 5/026; A61F 5/03; A61F 2250/001; A61F 5/01; A61F 2210/0076; A61F 13/148; A61F 13/00038; A61F 2007/0024; A61F 2007/0231; A61F 5/05; A61F 5/3715; A61F 5/0102; A61F 5/0193; A61F 13/145; A61F 2005/0183; A61F 5/3784; A61F 5/058; A61F 5/37; A41D 13/0531; A41D 13/0015; A41D 31/185; A41D 13/0512; A41D 13/0525; A41D 13/1245; A41D 19/01582; A41D 31/18; A41D 13/05; A41D 1/04; A41D 2300/32; A41D 2300/322; A41D 2300/324; A41D 2300/326; A41D 2300/328; A41D 2300/33; A41D 2300/332; A41D 2400/32; A41B 11/02; A63B 23/12; D04B 21/20
See application file for complete search history.

(56) References Cited

U.S. PATENT DOCUMENTS

| | | | |
|---|---|---|---|
| 6,440,094 | B1 | 8/2002 | Maas |
| 7,842,000 | B2 | 11/2010 | Lai |
| 7,871,388 | B2 | 1/2011 | Brown |
| 8,910,317 | B2 | 12/2014 | Decker |
| 9,452,078 | B2 | 9/2016 | Waeger |
| 2005/0197607 | A1 | 9/2005 | Brown |

(Continued)

*Primary Examiner* — Ophelia A Hawthorne
(74) *Attorney, Agent, or Firm* — Gregory M. MacDonald, Esq.

(57) ABSTRACT

The present invention relates generally to a garment for improving body posture that is lightweight, comfortable, discrete, adjustable, and easy to use, while requiring very little material with a low manufacturing cost. The present invention has scapular straps that are made of elastic fabric. One end of the scapular straps connect to a hook-and-loop panel near the waistline on the front of the garment, and the other end of the scapular straps connect to the back of the garment near the shoulder region. The invention has neither an elastic waist band, shoulder pads, nor straps that surround the shoulder and the arm. Since there are no straps surrounding the shoulder, the invention not only allows shorter straps to be used, but also prevents any seams from showing on the front of the garment. This allows the wearer to discreetly wear the posture correcting garment.

18 Claims, 7 Drawing Sheets

(56) References Cited

U.S. PATENT DOCUMENTS

2012/0316483 A1 12/2012 Waeger
2015/0040286 A1* 2/2015 Schultz .................... A41D 1/00
2/88

* cited by examiner

POSTURE SAVER

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR

Not Applicable

BACKGROUND

Unless otherwise indicated herein, the materials described in this section are not prior art to the claims in this application and are not admitted to be prior art by inclusion in this section.

1. Field of the Invention

The present invention generally relates to a garment for improving body posture. More specifically, the present invention relates to a garment for improving body posture that is fully adjustable with straps that attach to the back inside of the garment at their proximal ends and that attach to the front outside of the garment at their distal ends.

2. Description of Related Art

The majority of posture braces available today are built with the primary function of retracting the shoulders and adducting the scapulae, which are commonly referred to as the shoulder blades. These devices usually have straps that surround the front of the shoulders so that when the straps are pulled, the shoulders are pulled backwards and the scapulae are brought closer to each other. This can be a source of discomfort, because when the straps are in tension, they may rub and cause friction on the shoulders. This is especially irritating when the upper extremities are moved upward and around. From a biomechanical viewpoint, devices in the prior art do not achieve a true neutral spinal posture. Also, in the prior art, shoulder straps typically extend around the front of the shoulder, which not only causes a pressure point at the front of the shoulder, but also causes a noticeable protuberance through a shirt worn over such a device.

Devices for improving body posture are typically cumbersome to use, require a large amount of material, and have a high manufacturing cost. These devices also typically cause pressure points that make them uncomfortable. In addition, these devices make it obvious to a third person that the user is wearing a posture correcting device. Furthermore, these devices are typically heavy and have limited adjustments.

Thus, there is a need for a device that improves posture that is inexpensive, easy to use, lightweight, comfortable, discreet, and adjustable, while requiring a minimal amount of material with a low manufacturing cost. The device described in this patent application fulfills at least one of these needs or creates other utility.

BRIEF SUMMARY OF THE INVENTION

It is a principal object to solve at least one of the disadvantages with other attempted solutions or to create other utility by providing a garment for improving posture that is lightweight, comfortable, discrete, adjustable, and easy to use, while requiring very little material with a low manufacturing cost.

The garment of the present invention avoids at least one of these disadvantages, since it has the negative limitation that its straps do not travel around the front of the shoulders. As a result, the garment of the present invention neither creates a pressure point on the front of the wearer's shoulder, nor a protuberance through a shirt worn over the garment or through the garment itself. Instead, the scapular straps of the garment of the present invention connect to the inside back of the garment, which evenly pulls the material of the garment across the entire front surface area of the shoulder. Thus, there are no pressure points, because the tension from the scapular straps cause the garment to evenly distribute the force over the front of the shoulders. Also, the garment allows for complete freedom of movement of the upper extremities.

Since there are no straps surrounding the front of the shoulders, the invention also has a significant distinction from the prior art in that it allows shorter straps to be used. Also, since no part of the scapular straps are in the front of the shoulders, the garment can be worn without a third party knowing that the user is wearing a posture correcting device. This may cause the user to be more likely to wear the garment, because it eliminates the embarrassment that a user may feel in wearing a posture correcting garment. The garment has scapular straps where the tension may be fully adjustable with elastic fabric, a buckle, or another adjustment system. In at least one embodiment, the scapular straps may be sewn to the back inside of the garment at their proximal ends, so that the distal ends may be freely attached or detached from the front outside of the garment. The proximal ends of the scapular straps may be connected to the inside back of the garment using a connection mechanism selected from the group consisting of sewn threads, buttons, snaps, and hook-and-loop fasteners such as Velcro.

Also, the garment avoids at least one of the disadvantages of the prior art, since it also has the negative limitation that its straps do not connect together at the point where they intersect. This allows the straps to be independently adjusted for the individual amount of tension needed for each shoulder to allow for the correct posture for each individual. When the scapular straps of the garment are pulled in tension, the spine is extended as it is straightened backwards. This positions the lumbar spine in lordosis, which is an inward curvature of the spine also known as "hollowed forward". Thus, the garment achieves proper neutral posture for the wearer effortlessly and comfortably.

In addition, the garment avoids at least one of the disadvantages of the prior art, since it also has the negative limitation that the garment does not have an elastic waist band. An elastic waist band is uncomfortable and unsightly in that it takes away from a clean sleek look of the garment. The elastic waist band is also an added expense to supply and install. In addition, the elastic waist band may make it obvious to a third person that the user is wearing a posture correcting device.

Furthermore, the garment avoids at least one of the disadvantages of the prior art, since it also has the negative limitation that the garment does not have shoulder pads. Shoulder pads are an added expense to supply and install. Also, shoulder pads may make it obvious to a third person that the user is wearing a posture correcting device.

Overall, the invention also has the negative limitations that the garment has neither an elastic waist band, shoulder pads, straps that surround the front of the shoulders, nor straps that connect together at the point where they intersect, which allows the straps to be adjusted independently with the necessary amount of tension to allow the correct posture for each person.

The invention may have scapular straps made of an elastic fabric so that the amount of tension may be fully adjusted. The scapular straps may also be transferred between garments. The distal and proximal ends of the scapular straps may comprise a panel made of hook-and-loop material, such as Velcro. As a result, the garment improves posture, while being lightweight, comfortable, discrete, adjustable, easy to use, inexpensive, and requiring very little material.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
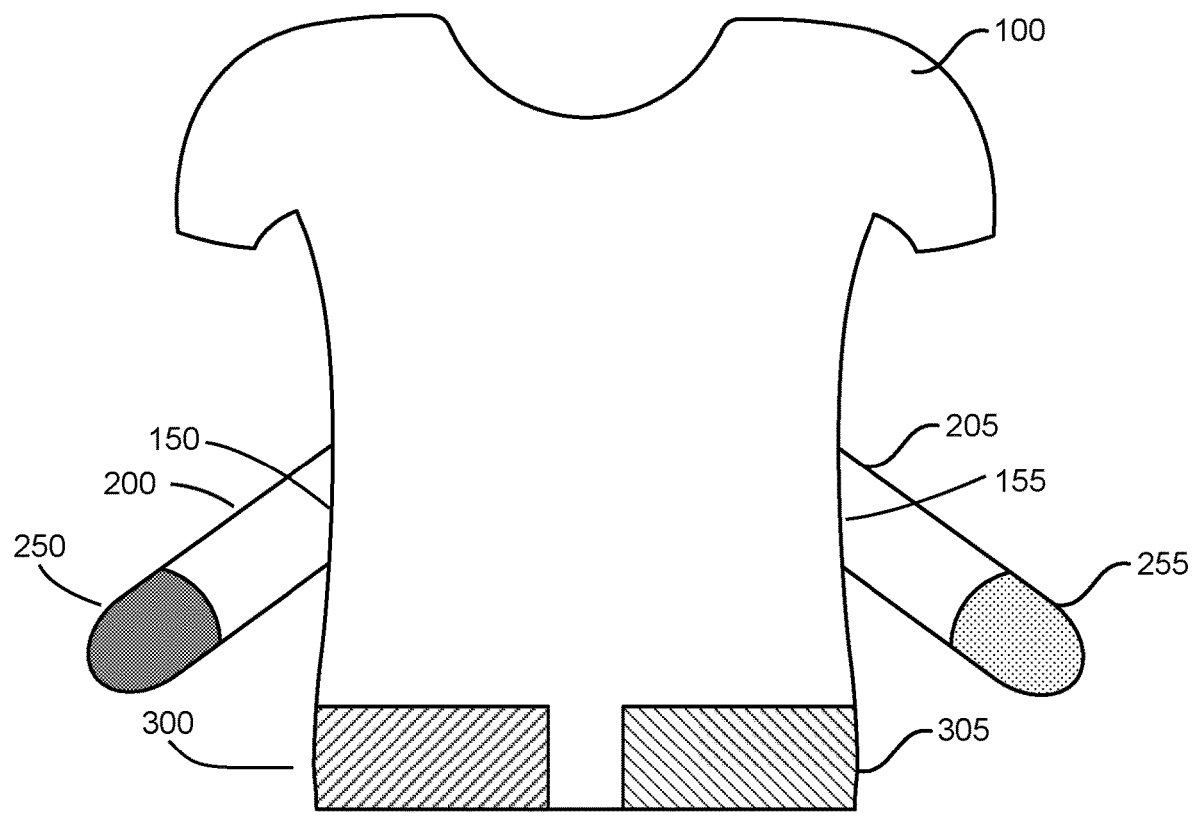
FIG. 1 is a front view of the present invention, where the distal ends of the scapular straps are shown with fastening panels near the waistline in which at least one of the embodiments of this invention is implemented.

It is to be understood that this invention is not limited to any particular embodiment described, which may vary. Also, it is to be understood that the terminology used herein is for the purpose of describing particular embodiments only, and is not intended to be limiting, since the scope of this invention will be limited only by the appended claims.

In the following detailed description, numerous specific details are set forth in order to explain and provide a thorough understanding of the present invention. However, it is apparent that the present invention may be practiced without all of these specific details. Thus, all illustrations of the drawings are for the purpose of describing versions of the present invention, and are not intended to limit the scope of the invention.

In the following section, the present invention is described fully by referencing the details in the enclosed drawings, which illustrate certain embodiments of the invention. The numbers shown in this specification refer to the corresponding numbers in the enclosed drawings. The terminology used is to describe the particular embodiment shown and is not intended to limit the scope of the invention. The invention may also be embodied in many other forms in addition to the embodiments shown. Thus, the embodiments shown should not be construed as limiting, but rather, to allow a thorough and complete description of the disclosure that conveys the scope of the invention to a person comprising ordinary skill in the art in the field of this invention. Therefore, for the terms used herein, the singular forms "the," "a," and "an" are intended to include the plural forms as well as the singular forms, unless the context clearly indicates otherwise. The term "and" includes any and all combinations of one or more of the associated listed items. As used herein, the terms "comprising" and "comprises" when used in this specification, identify specific steps, integers, operations, features, components, and elements, but do not preclude the presence or addition of one or more other steps, operations, features, components, and elements. In addition, the features, components, and elements referenced may be exaggerated for clarity.

Unless otherwise defined, all scientific terms, technical terms, or other terms used herein have the same meaning as the term that is understood by one having ordinary skill in the art in the field of this invention. It is also understood that these terms, including their dictionary meaning, should be understood as having the meaning, which is consistent with their definitions in the related relevant art. In addition, the present disclosure is not to be interpreted in an idealized or overly formal sense unless expressly stated so herein. Constructions or functions that are well known in the art may not be fully described in detail for brevity.

In describing the invention, it is understood that a number of steps and methods may be disclosed. Each of these may have individual benefit. Also, each may be used in conjunction with at least one or more of the disclosed steps and methods. Therefore, this description will refrain from stating each and every possible combination of the individual steps and methods for the sake of brevity. Regardless, the specification and related claims should be understood with the combinations that are entirely within the scope of the claims and inventions.

The disclosure in this invention are examples of how it may be implemented and are not intended to limit the scope of the invention to the specific embodiments shown in the accompanying drawings or the description provided herein.

The present invention will now be described by example in the following paragraphs by referencing the accompanying drawings, which represent embodiments and alternative embodiments. All illustrations are for the purpose of describing selected versions of the present invention and are not intended to limit the scope of the present invention.

The garment of the present invention prevents the wearer from bending forward in an inappropriate manner. It can be used whether one is sitting at a desk, working on a car, or engaging in other activities, such as performing surgery. The garment of the present invention also acts as an early warning system by applying tension, which may dramatically improve one's postural awareness. The garment continuously inhibits the wearer's trunk from slouching, and substituting instead the correct postural response, so that the brain will ultimately be "reprogrammed" to make sure that the trunk is always bending with a proper neutral posture. The garment improves posture while being lightweight, comfortable, discrete, adjustable, and easy to use with very little material and a low manufacturing cost.

FIG. 1 is a front view of the present invention, where the garment 100 comprises an outside front comprising a right-hand side and a left-hand side, an inside front comprising a right-hand side and a left-hand side, an outside back comprising a right-hand side and a left-hand side, an inside back comprising a right-hand side and a left-hand side, a left-hand side, and a right-hand side. Attached to the garment 100 are scapular straps 200 and 205. These scapular straps may have fasteners 250 and 255, respectively, on one or both sides of the distal ends of the scapular straps 200 and 205.

Figure 3:
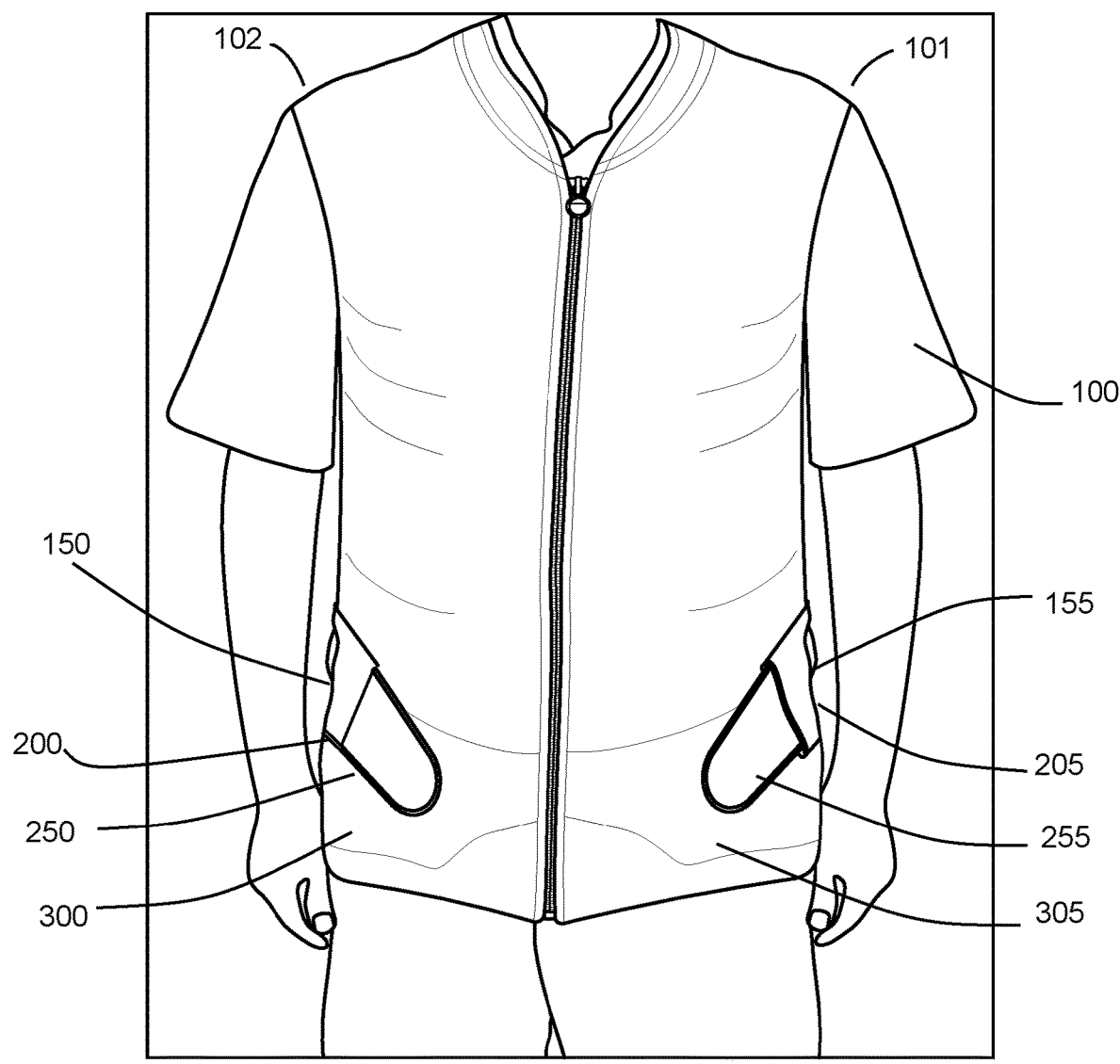
FIG. 3 is a front view of the present invention, where the scapular straps are shown connected to the front of the garment in which at least one of the embodiments of this invention is implemented.

FIG. 3 shows that the garment 100 may be worn like a vest for improving body posture. The garment 100 comprises a left-hand side waist panel 305 on its left-hand side 101. The left-hand side waist panel 305 has an outer side and an inner side. The inner side of the left-hand side waist panel 305 connects to the outside front of the garment 100 on the left-hand side of the waist. The outer side of the left-hand side waist panel 305 allows for a connection to the distal end 255 of a right scapular strap 205.

Also, as shown in FIG. 3, the garment 100 comprises a right-hand side waist panel 300. The right-hand side waist panel 300 on the right-hand side 102 of the garment 100 has an outer side and an inner side. The inner side of the right-hand side waist panel 300 connects to the outside front of the garment 100 on the right-hand side of the waist. The outer side of the right-hand side waist panel 300 provides a connection to the distal end 250 of the left scapular strap 200.

In addition, as shown in FIG. 3, the garment 100 comprises a left slot 155. The left slot 155 is on the left-hand side of the garment 100, and allows the right scapular strap 205 to pass through the left slot 155. Similarly, a right slot 150 on the right-hand side of the garment 100, allows the left scapular strap 200 to pass through.

As shown in FIG. 1, the scapular straps 200 and 205 may be either made of an elastic fabric or adjusted in length with an adjuster or variable length buckle. The elastic fabric may be comprised of rubber, latex, bungee, Lycra, spandex, natural fibers, synthetic fibers, or another elastomeric material.

As shown in FIG. 1, fasteners 250 and 255 may be comprised of the hook part of a Velcro fastener, while the corresponding fastener 300 and 305 may be comprised of the loop part of a Velcro fastener. In addition to Velcro, the fasteners may be comprised of buttons, snaps, buckles, zippers, clips, claps, hooks, carabiners, etc.

Also, as shown in FIG. 1, the inner side of the left waist panel 305 and the inner side of the right waist panel 300 may connect to the garment 100 with a fastener selected from a group consisting of at least one hook-and-loop fastener, pin, rivet, staple, clamp, clip, hook, anchor, tie, ring, band, crimp, adhesive, zipper, and sewn thread. Similarly, the outer side of the left waist panel 305 and the outer side of right waist panel 300 may connect to the distal ends 255 and 250, respectively, of the scapular straps 205 and 200, respectively, with a fastener selected from a group consisting of at least one hook-and-loop fastener, pin, rivet, staple, clamp, clip, hook, anchor, tie, ring, band, crimp, adhesive, zipper, and sewn thread.

Figure 2:
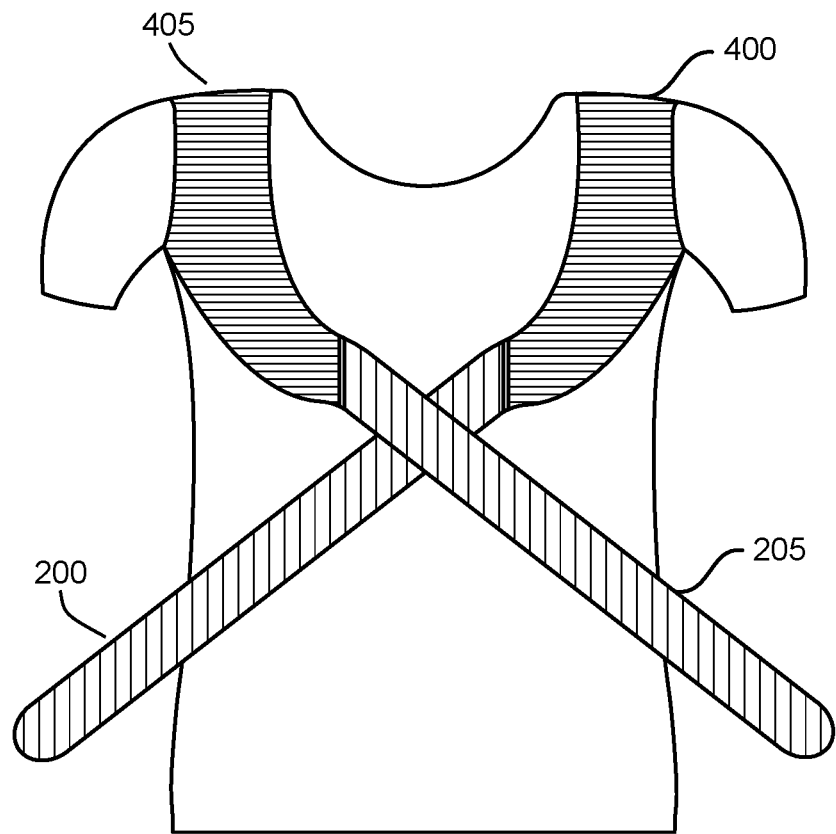
FIG. 2 is a back view of the present invention, where the proximal ends of the scapular straps are shown attached near the inside back scapula region, and the distal ends of the scapular straps are shown in which at least one of the embodiments of this invention is implemented.

FIG. 2 shows the back inside of the garment 100. The scapular straps 200 and 205 apply tension to the back of the garment 100 near the scapula regions 400 and 405, respectively, to pull the shoulders rearward for improving body posture. The proximal end of the scapular straps 200 and 205 may connect to the back of the garment 100 with a connection selected from a group consisting of at least one pin, rivet, staple, clamp, clip, hook, anchor, tie, ring, band, crimp, adhesive, zipper, and sewn thread.

As shown in FIG. 2, the garment 100 comprises a left scapular strap 200 with a proximal end and a distal end. The proximal end of the left scapular strap 200 connects to the inner side of the left scapular panel 400. As shown in FIG. 1 and FIG. 3, the distal end of the left scapular strap 200 passes through right slot 150 and connects to the outer side of the right-hand side waist panel 300.

Similarly, as shown in FIG. 2, the garment comprises a right scapular strap 205, with a proximal end and a distal end, where the proximal end connects to the inner side of the right scapular panel 405. Also, as shown in FIG. 1 and FIG. 3, the distal end of the right scapular strap 205 passes through the left slot 155 and connects to the outer side of the left-hand side waist panel 305.

The scapular straps 200 and 205 may be constructed of an elastic fabric so that the amount of tension is fully adjustable. In at least one embodiment, the scapular straps 200 and 205 may only be free at the distal ends, while the proximal ends may be directly connected to the back of the garment 100 using a connection mechanism selected from the group consisting of sewn thread, buttons, snaps, and hook-and-loop fasteners such as Velcro.

As shown in FIG. 2, the garment 100 comprises a left scapular panel 400 comprising an outer side and an inner side, wherein the outer side connects to the inside back of the garment 100 in the region of the left scapula. The inner side of the left scapular panel 400 connects to the proximal end of the left scapular strap 200.

Also, as shown in FIG. 2, the garment 100 comprises a right scapular panel 405 comprising an outer side and an inner side, wherein the outer side of the right scapular panel 405 connects to the inside back of the garment 100 in the region of the right scapula, and the inner side of the right scapular panel 405 connects to the proximal end of the right scapular strap 205.

In addition, as shown in FIG. 2, the outer side of the left scapular panel 400 and the outer side of right scapular panel 405 may connect to the garment 100 with a fastener selected from a group consisting of at least one hook-and-loop fastener, pin, rivet, staple, clamp, clip, hook, anchor, tie, ring, band, crimp, adhesive, zipper, and sewn thread. Similarly, the inner side of the right scapular panel 405 and the inner side of left scapular panel 400 connect to a scapular strap with a fastener selected from a group consisting of at least one hook-and-loop fastener, pin, rivet, staple, clamp, clip, hook, anchor, tie, ring, band, crimp, adhesive, zipper, and sewn thread.

Figure 5:
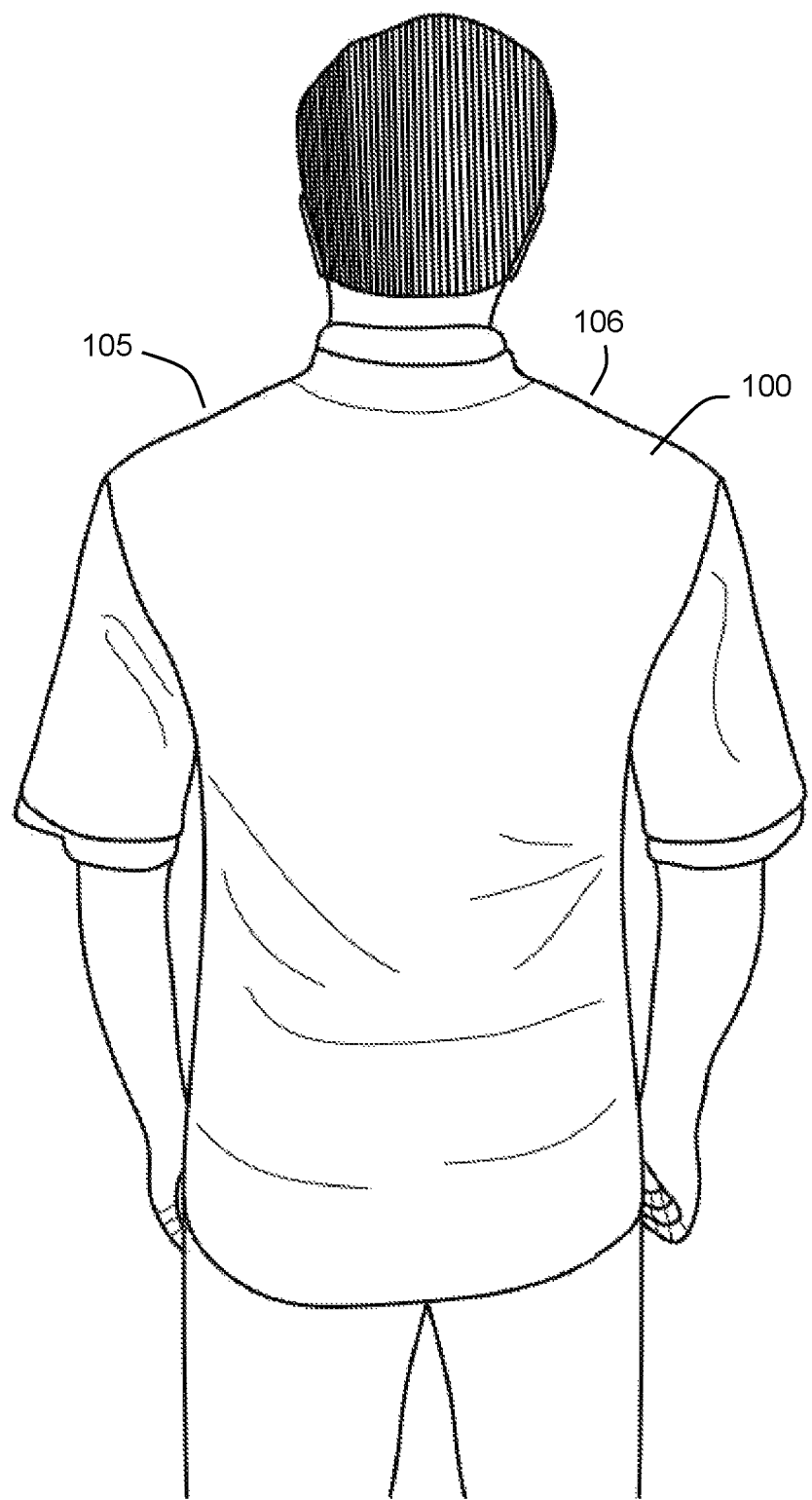
FIG. 5 is a view of the outside back of the present invention, where the scapular straps are not visible, since they are hidden on the inside of the garment in which at least one of the embodiments of this invention is implemented.

As shown in FIG. 2, the left scapular panel 400 and the right scapular panel 405 are only present on the back inside of the garment 100. As shown in FIG. 5, there is no connecting region on the back outside of the garment 100. Also, as shown in FIG. 3, there is no connecting region on the front of the garment 100. Since there are no scapular straps surrounding the front of the shoulder, the invention allows for relatively short scapular straps 200 and 205 to be used as compared to other garments. Also, by connecting the scapular straps 200 and 205 to only the back inside of the garment 100, any seams or other elements are prevented from showing through the front of the garment 100. This prevents a third person, who views the garment 100 from either the front or the back, from knowing that the user is wearing a garment 100 that is an orthotic garment. This allows the user to discreetly wear the posture correcting garment 100 without others knowing that the user is wearing an orthotic garment.

The invention has the negative limitations that the garment has neither an elastic waist band, shoulder pads, straps that surround the front of the shoulders or the arms, nor straps that connect together at the point where they intersect, which allows the straps to be independently adjusted for the amount of tension needed to allow the correct posture in each individual. The invention also has the negative limitations that the garment 100 has no exposed straps or other indications that it is a posture correcting garment when viewed from the backside. Thus, there is no indication to others that the user is wearing an orthotic garment 100.

Since the invention has the negative limitation that there are no straps surrounding the shoulder, the invention has a significant distinction from the prior art, because shorter scapular straps 200 and 205 may be used. Also, the lack of straps 200 and 205 surrounding the shoulder prevents any seams from showing through on the front of the garment, which allows the user to hide the fact that he is wearing a posture correcting garment 100.

As shown in FIG. 2, the garment 100 has two bands of fabric. One is in the region of the left scapular panel 400, and the other is in the region of the right scapular panel 405. These panels connect to the scapular straps 200 and 205, respectively. The proximal ends of these scapular straps 200 and 205 crisscross in the back. As shown in FIG. 3, the distal ends 250 and 255 of these straps 200 and 205, respectively, attach to the outside front of the garment 100 at the lower abdomen area at right waist panel 300 and left waist panel 305, respectively. The attachments on the distal ends 250 and 255 may be made with one side of a hook-and-loop material, while the right waist panel 300 and left waist panel 305 may be made with the opposite side of the hook-and-loop material.

Also, as shown in FIG. 3, the angle of the crisscross of the scapular straps 200 and 205 wrap around a wearer's flanks apply a slight soothing pressure to the wearer. Wearers have described the garment 100 as like being pleasantly hugged, because of the compression caused by the scapular straps 200 and 205 around the wearer's lower back area and flanks.

FIG. 3 is a front view of the garment 100 of the present invention, where the distal ends 250 and 255 of scapular straps 200 and 205, respectively, are shown connected to the front of the garment 100 on the outer sides of the right waist panel 300 and left waist panel 305, respectively. In addition, slots 150 and 155 are shown, where the scapular straps 200 and 205 pass through.

In at least one embodiment of the present invention, as shown in FIG. 3, the garment 100, the slots 150 and 155, the scapular straps 200 and 205, the fastener 250 and 255 at the ends of the scapular straps 200 and 205, and the corresponding waist panels 300 and 305 are all the same color. Because these are all the same color, when a third person views the user wearing the garment 100, there is little to no indication the user is wearing an orthotic or posture correcting garment.

Figure 4:
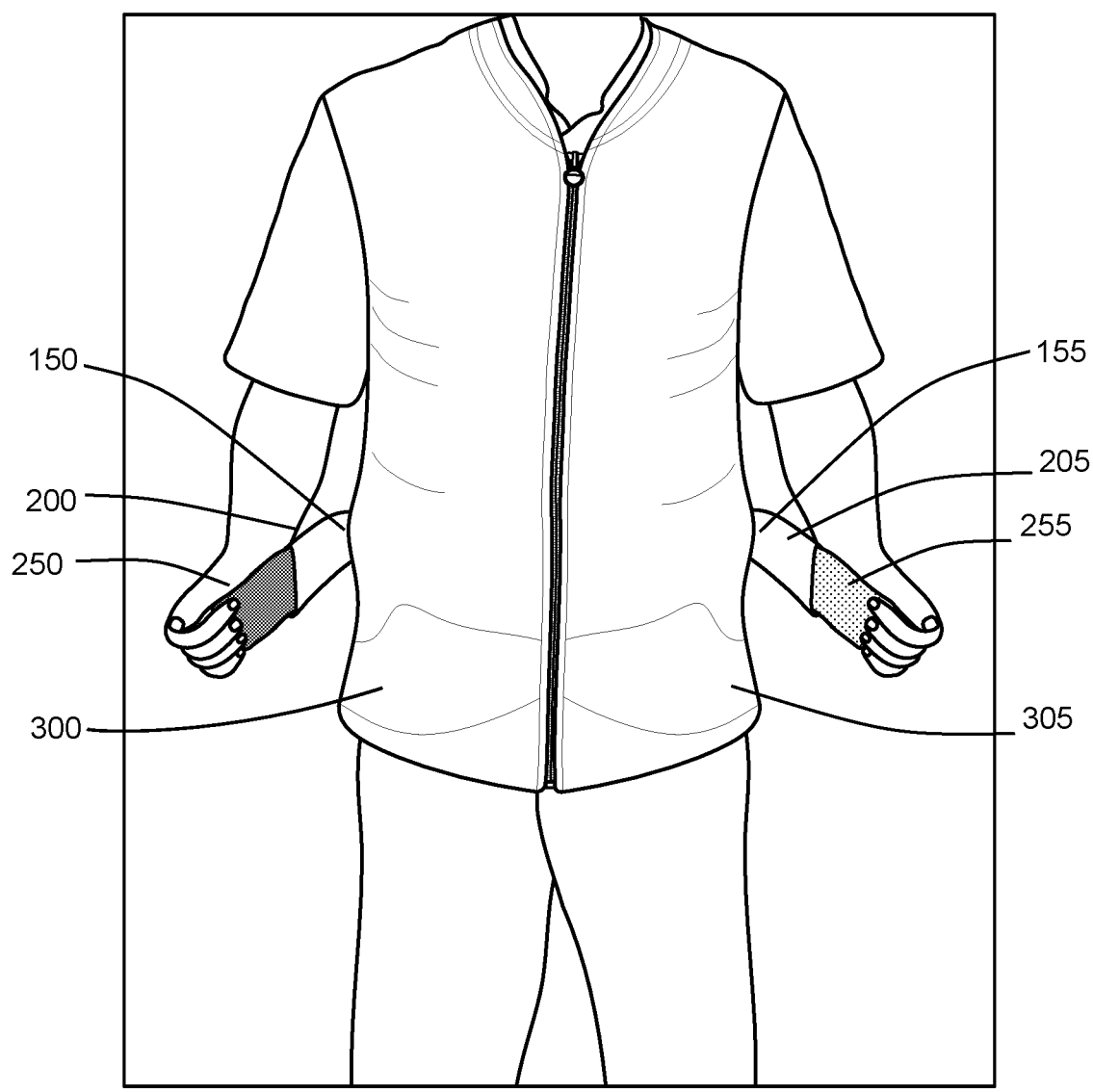
FIG. 4 is a front view of the present invention, where the scapular straps are shown disconnected from the front of the garment in which at least one of the embodiments of this invention is implemented.

FIG. 4 is a front view of the garment 100, where the scapular straps 200 and 205 are shown disconnected from the right waist panel 300 and left waist panel 305 on the front of the garment 100. Also, the slots 150 and 155 are shown, where the scapular straps 200 and 205 pass through. In addition, as shown in FIG. 4, when the scapular straps 200 and 205 are pulled forward, the shoulders retract, meaning that they are pulled backwards. When the shoulders are retracted, the spine is automatically extended, meaning that it is straightened back into a neutral position. Thus, the garment 100 positions the trunk of the user in a perfectly neutral position. The amount of tension that the garment 100 applies to the user's shoulders can be adjusted by the user pulling the scapular straps 200 and 205 to a desirable level, which ensuring that the garment 100 is in a comfortable position.

FIG. 5 is a view of the outside back of the garment 100 showing its left-hand side 105 and its right-hand side 106, where the scapular straps 200 and 205 are not visible, since they are hidden on the inside of the garment 100. Also, the left scapular panel 400 and the right scapular panel 405 are not visible, since they are hidden on the inside back of the garment 100.

Figure 6:
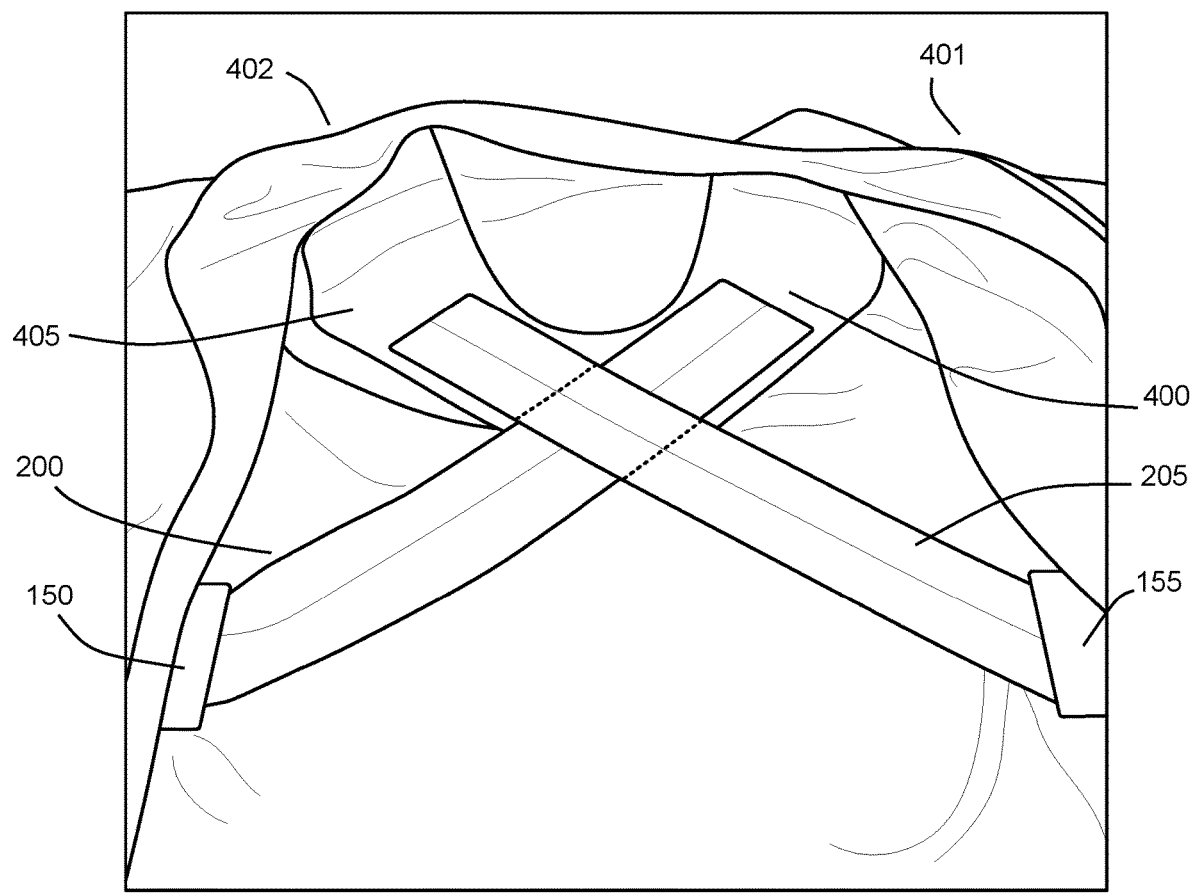
FIG. 6 is a view of the inside back of the present invention, showing the scapular straps on the inside back of the garment in which at least one of the embodiments of this invention is implemented.

FIG. 6 is a view of the inside back of the garment 100, showing the scapular straps 200 and 205 on the inside of the garment 100. The proximal ends of the scapular straps 200 and 205 connect to the inside back of the garment 100 on the inner left scapular panel 400 showing its left-hand side 401 and the right scapular panel 405 showing its right-hand side 402, respectively. In addition, shown are scapular straps 200 and 205 that pass through slots 150 and 155, respectively.

Figure 7:
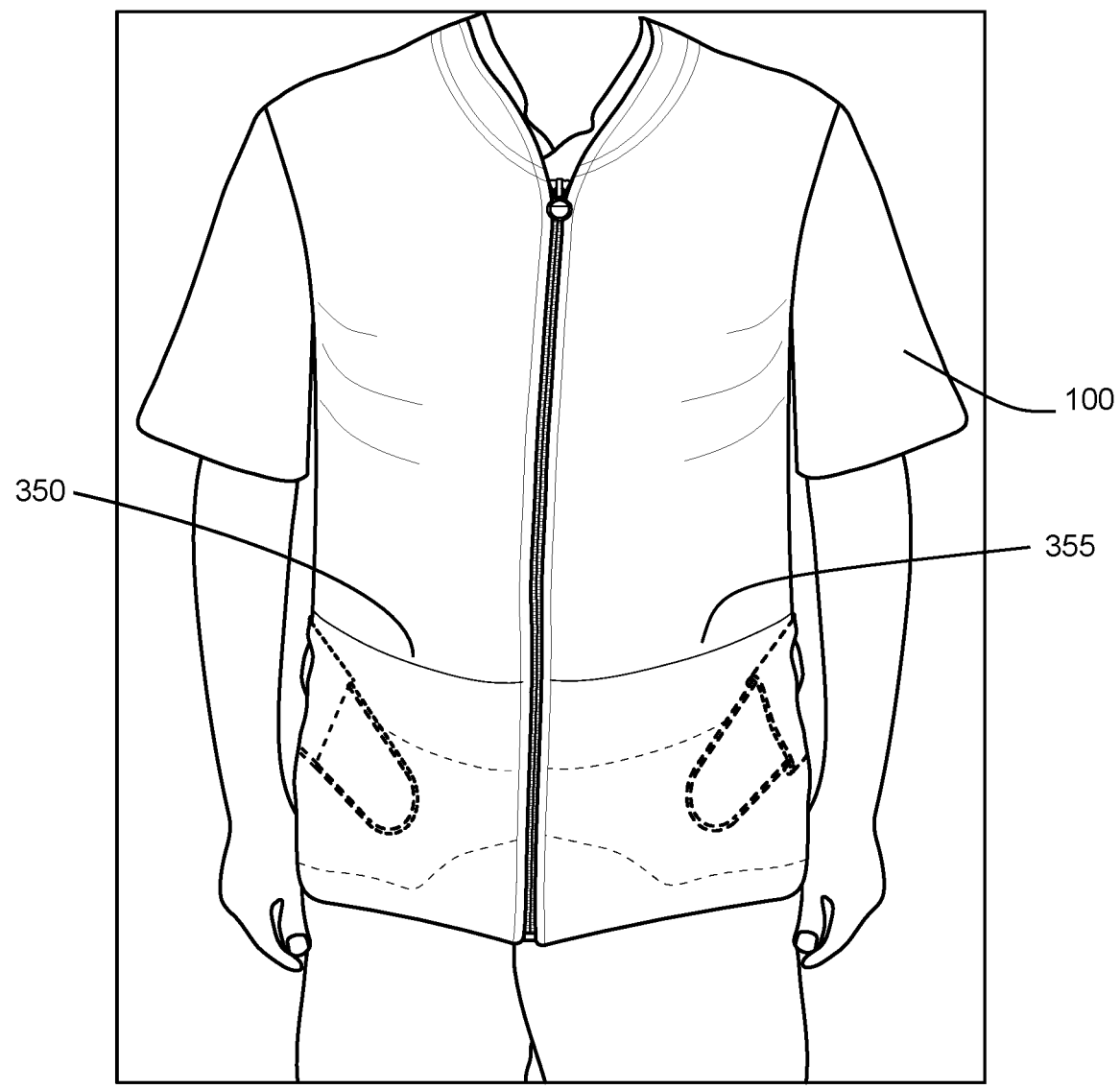
FIG. 7 is a front view of the present invention, where the scapular straps are hidden underneath at least one pocket on the front of the garment in which at least one of the embodiments of this invention is implemented.

As shown in FIG. 7, in at least one embodiment of the present invention, the garment 100 comprises right pocket 350 and left pocket 355 on the front of the garment 100. These pockets 350 and 355 not only allow a user to place his hands into, but that also hide fasteners 250 and 255, scapular straps 200 and 205, and their corresponding waist panels 300 and 305. Thus, these pockets 350 and 355 provide no indication to a third person that the user is wearing an orthotic garment when viewed from the front. Thus, the invention has the negative limitation that the garment 100 has no exposed straps when viewed by a third person.

The garment 100 may be manufactured to a variety of sizes for men, women, and children, so that it properly fits a person's torso and extends from approximately the waistline to the top of the shoulders. The scapular straps 200 and 205 may have a width of approximately ½-inch to approximately 6-inches, a thickness of approximately ⅛-inch to approximately 1-inch, a minimum length of approximately 8-inches to approximately 48-inches, and a maximum length of approximately 9-inches to approximately 72-inches. The fasteners 250 and 255 on the ends of the scapular straps 200 and 205, respectively, may have a width of approximately ½-inch to approximately 6-inches, a thickness of approximately ⅛-inch to approximately 1-inch, a length of approximately 1-inch to approximately 8-inches.

The garment 100 may be constructed of a material selected from a group consisting of cotton, polyester, plastic, nylon, polycotton, wool, yarns, cashmere, hemp, silk, alpaca, and linen. In at least one embodiment, the entire garment 100 may be constructed of the loop side of a hook-and-loop fastener. In this embodiment, the scapular straps 200 and 205 may be constructed where the entire inner side of the scapular straps 200 and 205 are constructed of the hook side of a hook-and-loop fastener, and the entire outer side of the scapular straps 200 and 205 are constructed of the loop side of a hook-and-loop fastener. In this embodiment, the hook side of the scapular straps 200 and 205 may be connected anywhere on the front of the garment 100, since the entire garment 100 is comprised of the loop side of a hook-and-loop fastener. This eliminates the need for waist panels 300 and 305 and the associated costs of manufacturing and installing these waist panels 300 and 305. This also eliminates a third person or casual observer from knowing that the user is wearing a posture correcting garment.

In at least one other embodiment, just the front outer side of the garment 100 may be constructed of the loop side of a hook-and-loop fastener. Similar to the above, in this embodiment, the entire inner side of the scapular straps 200 and 205 are constructed of the hook side of a hook-and-loop fastener, and the entire outer side of the scapular straps 200 and 205 are constructed of the loop side of a hook-and-loop fastener. In this embodiment, the hook side of the scapular straps 200 and 205 may be connected anywhere on the front of the garment 100, since the entire outer front side of the garment 100 is comprised of the loop side of a hook-and-loop fastener. This eliminates the need for separate waist panels 300 and 305 and the associated costs of manufacturing and installing these waist panels 300 and 305. This also eliminates a third person or casual observer from knowing that the user is wearing a posture correcting garment. In addition, the back side of the garment may be comprised of a less expensive material, since only the outer front side of the garment 100 is comprised of the loop side of a hook-and-loop fastener, which lowers the cost of the garment 100.

In at least one other embodiment, the scapular straps 200 and 205 may be constructed of a material selected from a group consisting of rubber, elastic, cotton, polyester, plastic, nylon, polycotton, wool, yarns, cashmere, hemp, silk, alpaca, and linen. The scapular straps 200 and 205 of the garment 100 may comprise a cross-sectional area selected from a group consisting of round, oval, elliptical, square, rectangular, circular, non-circular, oval, rounded rectangular, triangular, square, hexagonal, parallelogram, oblong, octagonal and combinations thereof.

All of these embodiments and the invention disclosed herein are intended to be within the scope herein disclosed. These and other embodiments of the invention will become readily apparent to those skilled in the art from the detailed description of the embodiments having reference to the attached figures, the embodiments not being limited to any particular embodiments disclosed. Also, the invention disclosed herein suitably may be practiced in the absence of any element which is not specifically disclosed herein.

What is claimed is:

1. A garment for improving body posture of a user, the garment comprising,
   a. an outside front comprising a right-hand side and a left-hand side;
   b. an outside back comprising a right-hand side and a left-hand side;
   c. an inside back comprising a right-hand side and a left-hand side;
   d. a left scapular strap comprising a proximal end and a distal end;
   e. a right scapular strap comprising a proximal end and a distal end;
   f. a left scapular panel on the inside back of the garment comprising an outer side and an inner side;
   g. a right scapular panel on the inside back of the garment comprising an outer side and an inner side;
   h. a left-hand side waist panel on the outside front of the garment comprising an outer side and an inner side;
   i. a right-hand side waist panel on the outside front of the garment comprising an outer side and an inner side;
   j. a left slot on the left-hand side of the garment, wherein the right scapular strap passes through the left slot;
   k. a right slot on the right-hand side of the garment, wherein the left scapular strap passes through the right slot;
   l. wherein the proximal end of the left scapular strap connects to the inner side of the left scapular panel and the distal end of the left scapular strap passes through the right slot and connects to the outer side of the right-hand side waist panel;
   m. wherein the proximal end of the right scapular strap connects to the inner side of the right scapular panel and the distal end of the right scapular strap passes through the left slot and connects to the outer side of the left-hand side waist panel;
   n. wherein the outer side of the left scapular panel connects to the inside back of the garment in a region adapted to the left scapula of the user, and the inner side of the left scapular panel connects to the proximal end of the left scapular strap;
   o. wherein the outer side of the right scapular panel connects to the inside back of the garment in the region adapted to the right scapula, and the inner side of the right scapular panel connects to the proximal end of the right scapular strap;
   p. wherein the inner side of the left-hand side waist panel connects to the outside front of the garment adapted to the left-hand side of the waist, and the outer side of the left-hand side waist panel connects to the distal end of the right scapular strap;
   q. wherein the inner side of the right-hand side waist panel connects to the outside front of the garment adapted to the right-hand side of the waist, and the outer side of the right-hand side waist panel connects to the distal end of the left scapular strap;
   r. wherein the outer side of left scapular panel and the outer side of right scapular panel connect to the garment with a fastener selected from a group consisting of at least one hook-and-loop fastener, pin, rivet, staple, clamp, clip, hook, anchor, tie, ring, band, crimp, adhesive, zipper, and sewn thread;
   s. wherein the inner side of right scapular panel and the inner side of left scapular panel connect to a scapular strap with a fastener selected from a group consisting of at least one hook-and-loop fastener, pin, rivet, staple, clamp, clip, hook, anchor, tie, ring, band, crimp, adhesive, zipper, and sewn thread;
   t. wherein the inner side of left waist panel and the inner side of right waist panel connect to the garment with a fastener selected from a group consisting of at least one hook-and-loop fastener, pin, rivet, staple, clamp, clip, hook, anchor, tie, ring, band, crimp, adhesive, zipper, and sewn thread;
   u. wherein the outer side of left waist panel and the outer side of right waist panel connect to a scapular strap with a fastener selected from a group consisting of at least one hook-and-loop fastener, pin, rivet, staple, clamp, clip, hook, anchor, tie, ring, band, crimp, adhesive, zipper, and sewn thread; and
v. wherein the left and right scapular straps are selected from a group consisting of a length adjuster, buckle, and elastic fabric.

2. The garment of claim 1, wherein the garment is constructed of a material selected from a group consisting of cotton, polyester, plastic, nylon, polycotton, wool, yarns, cashmere, hemp, silk, alpaca, and linen.

3. The left and right scapular straps of claim 1, wherein the left and right scapular straps are constructed of a material selected from a group consisting of rubber, elastic, cotton, polyester, plastic, nylon, polycotton, wool, yarns, cashmere, hemp, silk, alpaca, latex, bungee, spandex, natural fibers, synthetic fibers, linen, and other elastomeric materials.

4. The garment of claim 1, wherein the left and right scapular straps comprise a cross-sectional area selected from a group consisting of round, oval, elliptical, square, rectangular, circular, non-circular, oval, rounded rectangular, triangular, square, hexagonal, parallelogram, oblong, octagonal and combinations thereof.

5. The garment of claim 1, further comprising a pocket on the front of the garment that hides the ends of the scapular straps, the left-hand side waist panel, and the right-hand side waist panel.

6. The garment of claim 1, further comprising a fastener selected from a group consisting of at least one pin, clamp, clip, hook, anchor, tie, ring, band, crimp, adhesive, zipper, and hook-and-loop fastener to connect the left and right sides of the garment together.

7. The garment of claim 1, where the left and right scapular straps and left-hand side and right-hand side waist panel are all the same color, so when viewed, there is little to no indication to others that the user is wearing an orthotic garment.

8. The garment of claim 1, wherein the left and right scapular straps have a width of approximately ½-inch to approximately 6-inches, a thickness of approximately ⅛-inch to approximately 1-inch, and a maximum length of approximately 9-inches to approximately 72-inches.

9. The garment of claim 1 does not comprise an elastic waist band, shoulder pads, and straps configured to surround the shoulder or are in front of the shoulder, wherein the garment has no exposed straps or other garments when viewed from the backside or outer side of the garment to allow a user to hide the posture correcting garment when worn.

10. A garment for improving body posture of a user, the garment comprising,
a. an outside front comprising a right-hand side and a left-hand side;
b. an outside back comprising a right-hand side and a left-hand side;
c. an inside back comprising a right-hand side and a left-hand side;
d. a left scapular strap comprising a proximal end and a distal end;
e. a right scapular strap comprising a proximal end and a distal end;
f. a left-hand side waist panel on the outside front of the garment comprising an outer side and an inner side;
g. a right-hand side waist panel on the outside front of the garment comprising an outer side and an inner side;
h. a left slot on the left-hand side of the garment, wherein the right scapular strap passes through the left slot;
i. a right slot on the right-hand side of the garment, wherein the left scapular strap passes through the right slot;
j. wherein the proximal end of the left scapular strap connects to the inside back of the garment and the distal end of the left scapular strap passes through the right slot and connects to the outer side of the right-hand side waist panel;
k. wherein the proximal end of the right scapular strap connects to the inside back of the garment and the distal end of the right scapular strap passes through the left slot and connects to the outer side of the left-hand side waist panel;
l. wherein the inner side of the left-hand side waist panel connects to the outside front of the garment adapted to the left-hand side of the waist, and the outer side of the left-hand side waist panel connects to the distal end of the right scapular strap;
m. wherein the inner side of the right-hand side waist panel connects to the outside front of the garment adapted to the right-hand side of the waist, and the outer side of the right-hand side waist panel connects to the distal end of the left scapular strap;
n. wherein the inner side of left waist panel and the inner side of right waist panel connect to the garment with a fastener selected from a group consisting of at least one hook-and-loop fastener, pin, rivet, staple, clamp, clip, hook, anchor, tie, ring, band, crimp, adhesive, zipper, and sewn thread;
o. wherein the outer side of left waist panel and the outer side of right waist panel connect to a scapular strap with a fastener selected from a group consisting of at least one hook-and-loop fastener, pin, rivet, staple, clamp, clip, hook, anchor, tie, ring, band, crimp, adhesive, zipper, and sewn thread; and
p. wherein the left and right scapular straps are selected from a group consisting of a length adjuster, buckle, elastic fabric.

11. The garment of claim 10, wherein the garment is constructed of a material selected from a group consisting of cotton, polyester, plastic, nylon, polycotton, wool, yarns, cashmere, hemp, silk, alpaca, and linen.

12. The scapular strap of claim 10, wherein the at least one scapular strap is constructed of a material selected from a group consisting of rubber, elastic, cotton, polyester, plastic, nylon, polycotton, wool, yarns, cashmere, hemp, silk, alpaca, and linen.

13. The garment of claim 10, wherein the at least one scapular strap comprises a cross-sectional area selected from a group consisting of round, oval, elliptical, square, rectangular, circular, non-circular, oval, rounded rectangular, triangular, square, hexagonal, parallelogram, oblong, octagonal and combinations thereof.

14. The garment of claim 10, further comprising a pocket on the front of the garment that hides the ends of the left and right scapular straps, the left-hand side waist panel, and the right-hand side waist panel.

15. The garment of claim 10, further comprising a fastener selected from a group consisting of at least one pin, clamp, clip, hook, anchor, tie, ring, band, crimp, adhesive, zipper, and hook-and-loop fastener to connect the left and right sides of the garment together.

16. The garment of claim 10, where the left and right scapular straps and left-hand side and right-hand side waist panel are all the same color, so when viewed, there is little to no indication to others that the user is wearing an orthotic garment.

17. The garment of claim 10, where the left and right scapular straps have a width of approximately ½-inch to approximately 6-inches, a thickness of approximately ⅛-inch to approximately 1-inch, and a maximum length of approximately 9-inches to approximately 72-inches.

18. The garment of claim 10 does not comprise an elastic waist band, shoulder pads, and straps configured to surround the shoulder or are in front of the shoulder, which allows the straps to independently adjust an amount of tension to allow a correct posture in each individual, wherein the garment has no exposed straps or other garments when viewed from the backside or outer side of the garment, which allows the wearer to hide the posture correcting garment when worn.

\* \* \* \* \*